United States Patent [19]

Bacon

[11] Patent Number: 5,297,542
[45] Date of Patent: Mar. 29, 1994

[54] AEROSOL DISPENSING DEVICE

[75] Inventor: Raymond J. Bacon, 36 Down End Road, Drayton, Portsmouth PO6 1HU, England

[73] Assignee: Raymond J. Bacon, Portsmouth, England

[21] Appl. No.: 962,038

[22] Filed: Oct. 15, 1992

Related U.S. Application Data

[63] Continuation of Ser. No. 742,579, Aug. 7, 1991, abandoned, which is a continuation of Ser. No. 541,610, Jun. 21, 1990, abandoned.

[30] Foreign Application Priority Data

Jun. 22, 1989 [GB] United Kingdom .................. 8914383

[51] Int. Cl.⁵ ............................................ A61M 11/00
[52] U.S. Cl. .......................... 128/200.14; 128/200.23
[58] Field of Search ...................... 128/200.14, 200.16, 128/200.18, 200.23, 203.12, 205.24

[56] References Cited

U.S. PATENT DOCUMENTS

| 3,157,179 | 11/1964 | Paullus et al. ................. 128/200.23 |
| 3,565,070 | 2/1971 | Hanson et al. . |
| 3,605,738 | 6/1969 | Ciranna . |
| 3,826,413 | 7/1974 | Warren . |
| 4,648,393 | 3/1987 | Landis et al. ................. 128/200.23 |

FOREIGN PATENT DOCUMENTS

| 0232235 | 1/1987 | European Pat. Off. . |
| 2204799 | 11/1988 | United Kingdom . |

*Primary Examiner*—Edgar S. Burr
*Assistant Examiner*—Aaron J. Lewis
*Attorney, Agent, or Firm*—Reese Taylor

[57] ABSTRACT

A inhalation-actuable dispensing device is provided for dispensing a metered dose of medicament in aerosol form. The device comprises a compartment (6) for receiving a metered dose aerosol container (10) having an outlet tube (12) at one end. The device has a storage chamber (13; 120) which receives a metered dose from the container. The storage chamber (13; 120) has an outlet which is closed by a valve member (44; 124) under the pressure of the dose within the storage chamber. Inhalation by a user causes a dose releasing device (34, 40, 46; 138-140) to move the valve member to an open position.

15 Claims, 3 Drawing Sheets

AEROSOL DISPENSING DEVICE

This application is a continuation of application Ser. No. 742,579, filed Aug. 7, 1991, which is a continuation of Ser. No. 07/541,610, filed Jun. 21, 1990, now both abandoned.

This invention relates to a dispensing device which is particularly suited for dispensing and administering metered amounts of fluids. The principal use for such a device is in dispensing metered amounts of a medicament-containing liquid in aerosol form for inhalation therapy.

In particular the invention is concerned with a dispensing device of that type where the metered dose of the drug is administered in response to the inhalation of the patient.

Metered dose inhalers are well known in medicine for the treatment of, or alleviation of the effects of respiratory complaints, for example asthma, and generally comprise a pressurised aerosol dispensing container, removably mounted within a carrier, and means for actuating a valve within the container to cause release of a metered amount of the medicament-containing liquid to be released towards a chamber having a mouthpiece for use by the patient. The means for actuating the valve may be a manually operated trigger device, or the patient may simply press on the closed end of the container with a thumb or finger, but in either case the patient is intended to co-ordinate the actuation of the valve with inhalation in order to obtain the maximum benefit from the medicament.

Unfortunately, many patients needing this type of treatment are unable to co-ordinate their breathing with the manual actuation of the valve.

It is an object of the invention to provide a metered dose inhaler wherein the release of the aerosol medicament is actuated by the inhalation of the patient.

In one aspect of the invention there is provided an inhalation-actuable dispensing device for use with a pressurised aerosol dispensing container comprising: a receptacle for said container; means defining a storage chamber arranged to receive a metered dose from the container, and having an outlet; a valve means having a closed position in which, in use, it closes the outlet under pressure from the dose in the chamber, and an open position in which the outlet is open to allow the dose to leave the chamber and enter the outlet spout; an outlet spout through which a user can inhale; and a releasing device responsive to inhalation of a user to move said valve means to its open position.

In a preferred arrangement, response of the piston unit to inhalation causes actuation of a valve to release the stored medicament from the receiving and storage means into the mouthpiece.

Various embodiments of the invention will now be described by way of example only, with reference to the accompanying drawings, in which.

Figure 1:
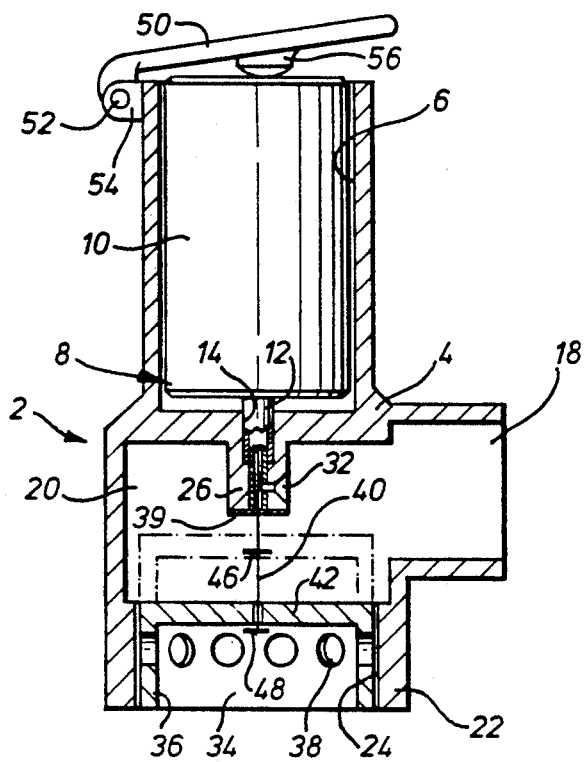
FIG. 1 is a view mainly in section of an inhalation device according to the invention.
Figure 2:
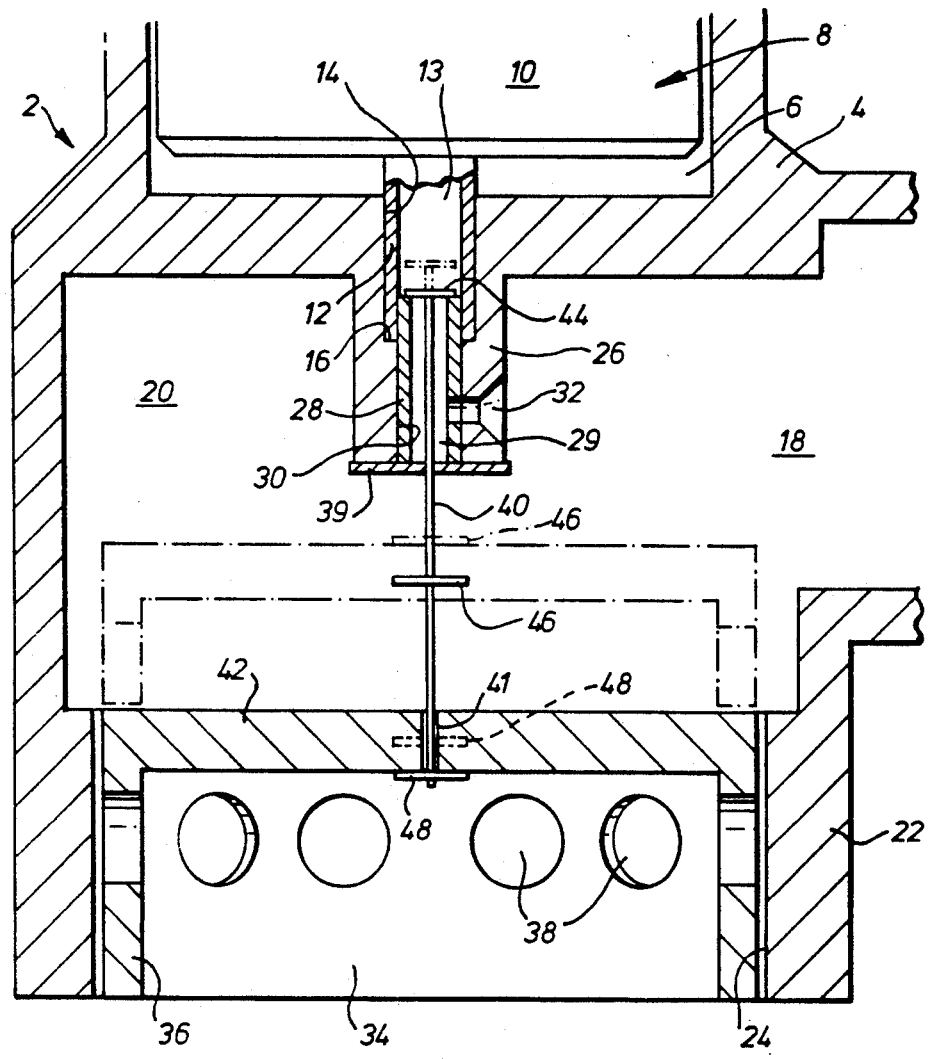
FIG. 2 is a section view to a larger scale of some parts of FIG. 1.

As seen in FIGS. 1 and 2, an inhalation device 2 includes a housing 4 having therein a compartment 6 for an aerosol medicament dispenser 8. The dispenser 8 includes a canister 10 and an outlet tube 12, details of which latter are clearly seen in FIG. 2.

The canister 10 contains a medicament suspended or dissolved in a liquid aerosol propellant, the medicament being suitable for inhalation therapy. The interior of the canister 10 communicates with the outlet tube 12 via an outlet valve (which is of conventional form and is not shown), the valve including a metering chamber. The tube 12 has a transfer port (not visible in the drawings) which when, and only when, the tube is moved inwardly with respect to canister 10, provides communication between the interior of the metering chamber and the interior of the tube.

The housing 4 is formed with a bore 14, coaxial with the compartment 6 and the outlet tube 12 fits within that bore, the outer end face of the tube being in contact with a shoulder 16 at the bottom of the bore 14.

The housing 4 has an outlet spout in the form of a mouthpiece 18 and a hollow interior portion 20. Coaxially with the compartment 6 and below the level of the mouthpiece 18 is a vertically depending short cylindrical part 22 formed with a bore 24.

A projection 26 extends into the hollow portion 20 and the bore 14 extends into the upper portion of that projection. A delivery tube 28 defining a delivery chamber 29 is located in a bore 30, coaxial with the bore 14 in the projection 26 and extends upwardly for a short distance above the shoulder 16 at the bottom of the bore 14. An outlet orifice 32 connects the chamber 29 with the interior portion 20 and the mouthpiece 18 of the housing 4.

Within the bore 24 of the housing is located a piston 34 having a skirt 36 and a top portion 42. A plurality of holes 38 extend through the skirt around its periphery.

Fixed by adhesive to the bottom of the projection 26 is a low friction sealing disc 39, and a length of very thin stiff wire 40 passes upwardly through the sealing disc, in frictional contact therewith, and freely through the hollow delivery tube 28. The wire also extends downwardly and passes freely through a hole 41 in the top portion 42 of the piston 34.

To the topmost end of the wire is fixed a valve head 44 which, when the inhaler is not in use, sits in sealing contact with the top face of the delivery tube 28 under the weight of the piston 34. Two discs 46 and 48 are fixed on the wire 40, one disc 46 being positioned around the middle point of the length of the wire, and the other disc 48 being positioned adjacent the lower end of the wire and below the portion 42 of the piston 34.

The canister 10 is slidable up and down in the compartment 6 and may be thus moved manually by direct digital pressure on the end of the canister, or a system of leverage or a screw arrangement may be provided. In the example shown in FIG. 1, a lever 50 is hinged about a pivot pin 52 fast in a bifurcated lug 54 on the housing, and a projection 56 can be pressed down onto the top of the canister 10 by rocking the lever manually.

In use, the patient presses the canister downwardly into the compartment 6 as just described, thus actuating the outlet valve within the canister. This causes a metered dose of medicament and propellant to pass via the metering chamber into the hollow chamber 13 defined within the outlet tube 12 above the delivery tube 28 which is at that stage sealed by the valve head 44. Sealing is effected by virtue of the fact that the propellant in the chamber 13 is at substantially above atmospheric pressure and thus forces the valve head 44 against the end of the tube 28. It is to be understood that the whole of the dose does not at this stage enter the chamber 13. This is because the chamber 13 is in communication with the metering chamber via the above mentioned transfer port, so that the dose is held partly in the chamber 13 and partly in the metering chamber, depending on the relative sizes thereof.

While continuing to hold the canister in its downward position, the patient places his mouth over the mouthpiece 18 of the housing and inhales through the mouth. Holding the canister in its downward position has the effect of preventing the dose held in the chamber 13 escaping through the transfer port. Inhalation by the patient generates a decrease in pressure within the hollow interior portion 20 of the housing which causes the piston 34 to move upwardly to the position shown in chain lines in FIG. 1 where its top face engages the disc 46, moving the wire 40 upwardly to disengage the valve head 44 from its sealing relationship with the top of the delivery tube 28. Because the cross-sectional area of the piston 34 is very large compared to the area of the valve head 44, a relatively small pressure difference across the piston is sufficient to overcome a much larger opposing difference across the valve head. The metered dose of medicament and propellant in the metering chamber of the dispenser outlet valve and in the chamber 13 passes into the delivery tube 28 and through the outlet orifice 32 where it mixes with air entering the hollow portion 20 of the housing through the holes 38 in the walls of the elevated piston 34. Thus, a metered dose of medicament is inhaled by the patient.

If desired, means (not shown) may be provided for holding the canister in its downward position during inhalation without requiring the patient to continue to press down on the lever 50, for example in the form of a 90 degree coarse helix turn screw.

In the above described embodiment the weight of the piston is sufficient to return the wire and valve head to their lowered position and yet sufficiently light in weight to be raised by the act of inhalation by the patient. The friction of the sealing disc 39 on the wire 40 is sufficiently limited to ensure very little resistance to axial movement of the wire, but adequate to cause effective sealing of the lower end of the delivery tube 28. It should be noted that it is not necessary for a high degree of sealing to be provided between the sealing disc 39 and the wire 40, since the metered dose is only in the region immediately above the sealing disc transiently on its way to the outlet orifice 32.

Alternatively, a flexible diaphragm may be used, this being secured e.g. by adhesive, around its peripheral margin to the bottom face of the projection 26, and to the wire 40. Sufficient flexure of the diaphragm would be obtained to allow the small amount of elevation necessary to raise the valve head 44 from its seating on the delivery tube.

Figure 2A:
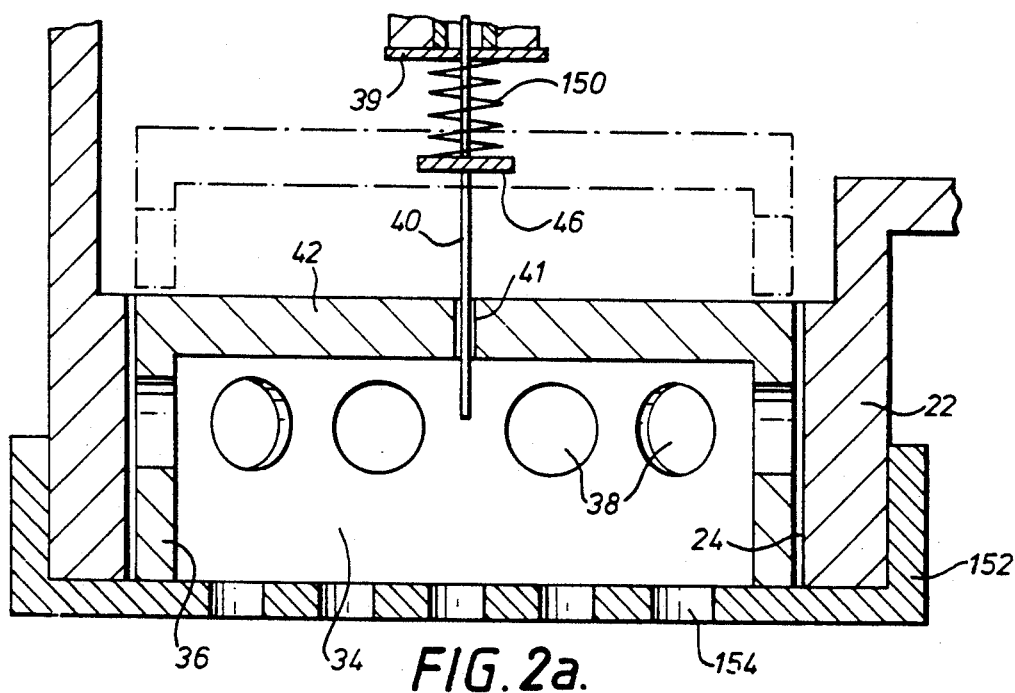
FIG. 2a is a view similar to FIG. 2, but showing a fragment of a modification thereof.

If it is found necessary, a light compression spring 150 may be interposed as shown in FIG. 2a between the sealing disc 39 and the disc 46 to bias the valve head towards its seating on the delivery tube. This ensures that the valve head is always seated on the delivery tube before the dispenser is actuated by the patient, thus eliminating the possibility that the first part of the dose entering the chamber 13 might escape past the valve head before the valve head had time to seal under the pressure in the chamber 13. It also ensures that the dose cannot leave the chamber 13 merely by the device being inverted after the dispenser is actuated. Were it not for the spring, this could occur by the piston falling towards, and striking, the disc 46.

If so desired, the piston 34 may be retained within the bore 24 by providing a grid, wire gauze or the like over the open end of the bore. This is shown in FIG. 2a, where there is an end cap 152 with air holes 154 therein. Alternatively, the lower face of the cylindrical part 22 may be provided with an inwardly directed annular rim which extends beneath the walls 36 of the piston. In either case, the piston 34 does not need to be attached to the wire 40, and the lower portion of the wire and the disc 48 can be omitted. However, the above mentioned compression spring is then needed to return the valve head 46 to its sealing position.

In another alternative arrangement, the cylindrical part 22 is provided with holes around its periphery and the piston is inverted, having its portion 42 at the bottom, but also being provided with holes 3 spaced around the upturned skirt. The holes in the cylindrical part are effectively sealed off by the continuous part of the skirt 36 when the piston is in its lowermost position. In this arrangement inhalation by the patient causes the piston to rise and when the holes in the skirt align with the holes in the cylindrical part 22, air flows through the aligned holes to the mouthpiece. In order to ensure alignment of the holes in the skirt with those in the cylindrical part a suitable spline arrangement may be provided between piston 34 and bore 24. Alternatively, the holes 38 may be interconnected by an annular groove formed in the outer surface of the skirt.

Figure 3:
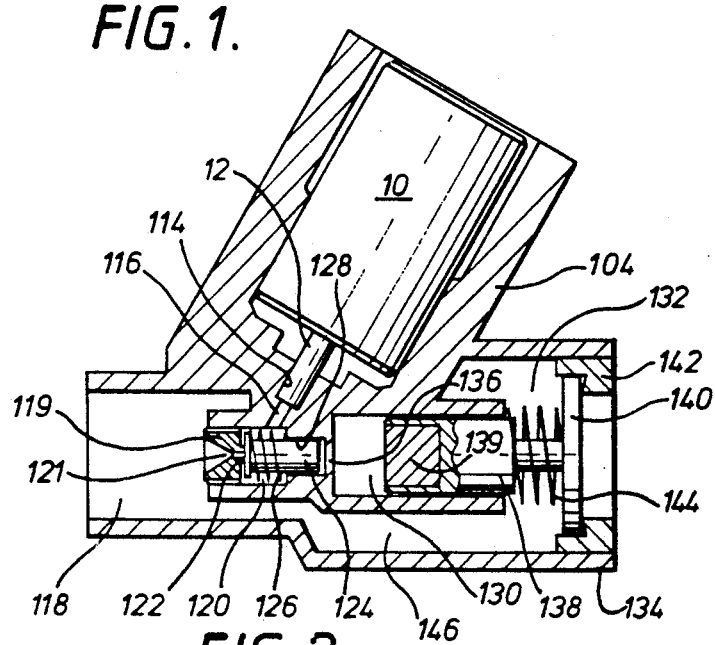
FIG. 3 is a section view of another embodiment of the invention.

In a further alternative arrangement, shown in FIG. 3, the intermediate chamber is loaded with a metered dose of medicament which is released into the mouthpiece by means of a magnetically actuated poppet valve which is activated by the inhalation of the patient.

As seen in FIG. 3, the canister 10 is located in a housing 104 and its outlet tube 12 extends into a bore 114 which is concocted by a small diameter hole 116 to an intermediate chamber 120. The chamber 120 is connected to the mouthpiece 118 by an outlet member 119 having an outlet orifice 121 surrounded by a valve seat 122. A poppet valve 124 is biassed towards the valve seat 122 by a light spring 126. The poppet valve 124 is slidable in a bore 128 formed in the housing 104 and a further bore 130 extends from a cavity 132 formed in a cylindrical part 134 of the housing towards the bore 128. The bores 128 and 130 are separated only by a very thin web. Within the bore 130 is a cylindrical part 138 of a piston unit which has a piston head 140 normally in engagement with a seating 142 and retained there by a light spring 144. The cavity 132 is connected to the mouthpiece by a passageway 146.

The poppet valve 124 and the cylindrical part 138 are made so that they can attract each other magnetically. For this purpose, the cylindrical part 138 has an element 139 which is a magnet or is of a magnetisable material, and the poppet valve includes a magnet or, provided the element 139 is a magnet, is of magnetisable material.

In operation, the canister is depressed as described earlier, to charge the intermediate chamber 120 with a metered dose of medicament and propellant. The patient then inhales through the mouthpiece 118 and this causes a drop in pressure within the cavity 132. The difference in pressures on either side of the piston head 140 is sufficient to overcome the action of the spring 144 and to cause the cylindrical part 138 with its element 139 to move further into the bore 130 until it contacts the web 136. The proximity of the element 139 acts to withdraw the valve 124 from its sealing position in contact with the valve seat 122 and the medicament mixes with air flowing past piston head 140 and is inhaled by the patient.

I claim:

1. An inhalation-actuable dispensing device for use with a pressurised aerosol dispensing container comprising:
   a) a receptacle for the pressurised aerosol dispensing container;
   b) means defining a storage chamber arranged in fluid communication with the pressurised aerosol dispensing container when received in said receptacle to receive a metered dose from the pressurised aerosol dispensing container, and having an outlet;
   c) an outlet spout in fluid communication with said outlet through which a user can inhale;
   d) valve means disposed between said container and said outlet spout and normally closing off said outlet from communication with said outlet spout under pressure from the dose in said storage chamber;
   e) a dose releasing device movable in response to inhalation of a user to engage said valve means and move said valve means toward said pressurised aerosol dispensing container and to its open position against the pressure from the dose in said storage chamber; and
   f) said dose releasing device being movable away from said pressurised aerosol dispensing container upon cessation of inhalation to return said valve means to its closed position.

2. A device according to claim 1, comprising means defining a bore for receiving an outlet tube of the pressurised aerosol dispensing container, and said storage chamber is defined at least partly within said outlet tube.

3. A device according to claim 1, wherein said dose releasing device comprises a piston one side of which is subjected to the pressure in said outlet spout and the other side of which is subjected to atmospheric pressure, said piston being movable in response to inhalation from a rest position to valve-opening position.

4. A device according to claim 3, wherein said piston is provided with at least one aperture therethrough, said aperture being substantially closed when said piston is in its closed position, and being open when said piston is in its valve-opening position.

5. A device according to claim 4 wherein said storage chamber communicates with said outlet spout via a delivery chamber and an outlet orifice, communication being controlled by said valve means.

6. A device according to claim 4 wherein said valve means and said dose releasing device are provided with means which are adapted to interact magnetically with one another when said dose releasing device responds to inhalation of the user, said interaction causing said valve means to its open position.

7. A device according to claim 3 wherein said valve means and said dose releasing device are provided with means which are adapted to interact magnetically with one another when said piston responds to inhalation of the user, said interaction causing said valve means to move toward said piston and to its open position.

8. A device according to claim 3 wherein said storage chamber communicates with said outlet spout via a delivery chamber and an outlet orifice, communication being controlled by said valve means.

9. A device according to claims 1 or 2, wherein said storage chamber communicates with said outlet spout via a delivery chamber and an outlet orifice, communication being controlled by said valve means.

10. A device according to claim 9, wherein said dose releasing device is connected to said valve means by an actuation member which passes into and through said delivery chamber.

11. A device according to claim 10, wherein said delivery chamber has an opening closed by an apertured sealing disc, and said actuation member passes in sliding contact through an aperture in the sealing disc.

12. A device according to claim 10, wherein said delivery chamber has an opening closed by a flexible diaphragm, and said actuation member passes through said flexible diaphragm and is sealed thereto.

13. A device according to claim 9, wherein one end of said delivery chamber extends into said outlet tube, and said valve means comprises a valve member which, in the closed position of the valve means, is urged against said end of said delivery chamber.

14. A device according to claims 1 or 2, wherein said valve means and said dose releasing device are provided with means which are adapted to interact magnetically with one another when said dose releasing device responds to inhalation of the user, said interaction causing said valve means to move toward said dose releasing device and to its open position.

15. A device according to claims 1 or 2, comprising means for returning said dose releasing device to its initial condition, after inhalation of the user.

* * * * *

UNITED STATES PATENT AND TRADEMARK OFFICE
CERTIFICATE OF CORRECTION

PATENT NO. : 5,297,542
DATED : March 29, 1994
INVENTOR(S) : Raymond J. Bacon

It is certified that error appears in the above-identified patent and that said Letters Patent is hereby corrected as shown below:

In the Abstract, line 1, delete "A" and substitute therefor ---An---;

In Column 4, line 19, delete "holes 3" and substitute therefor ---holes 38---; and In Column 4, line 39, delete "concocted" and substitute therefor ---connected---.

Signed and Sealed this

Sixth Day of September, 1994

Attest:

BRUCE LEHMAN

Attesting Officer

Commissioner of Patents and Trademarks